United States Patent [19]
Sillard

[11] Patent Number: 5,419,700
[45] Date of Patent: May 30, 1995

[54] REINFORCED JOINT FOR FITTING DENTAL APPLIANCES AND METHOD FOR FABRICATING SAME

[76] Inventor: Rannar Sillard, 206 Madison Ave., Lakewood, N.J. 08701

[21] Appl. No.: 140,744

[22] Filed: Oct. 22, 1993

[51] Int. Cl.⁶ .................... A61C 13/12; A61C 13/225
[52] U.S. Cl. .................................................. 433/172
[58] Field of Search .............. 433/172, 173, 174, 175, 433/176, 201.1

[56] References Cited

U.S. PATENT DOCUMENTS

| | | | |
|---|---|---|---|
| 3,748,739 | 7/1973 | Thibert | 433/173 |
| 5,007,833 | 4/1991 | Barbone | 433/172 |
| 5,052,928 | 10/1991 | Andersson | 433/172 |
| 5,064,374 | 11/1991 | Lundgren | 433/173 |
| 5,219,286 | 6/1993 | Hader | 433/172 |

FOREIGN PATENT DOCUMENTS 9100711 1/1991 WIPO ................................ 433/174

Primary Examiner—Cary E. O'Connor
Attorney, Agent, or Firm—Clifford G. Frayne

[57] ABSTRACT

A support structure for a dental implant appliance secured to the alveolar bone, the support structure shaped to the curvilinear contour of the portion of the jaw receiving the dental appliance, the support structure segmented by transverse cuts, each transverse cut having a divergent recess on opposing sides thereof for receipt of a complimentary recess plug in cooperation with investment solder to reattach the segments after fitting.

8 Claims, 3 Drawing Sheets

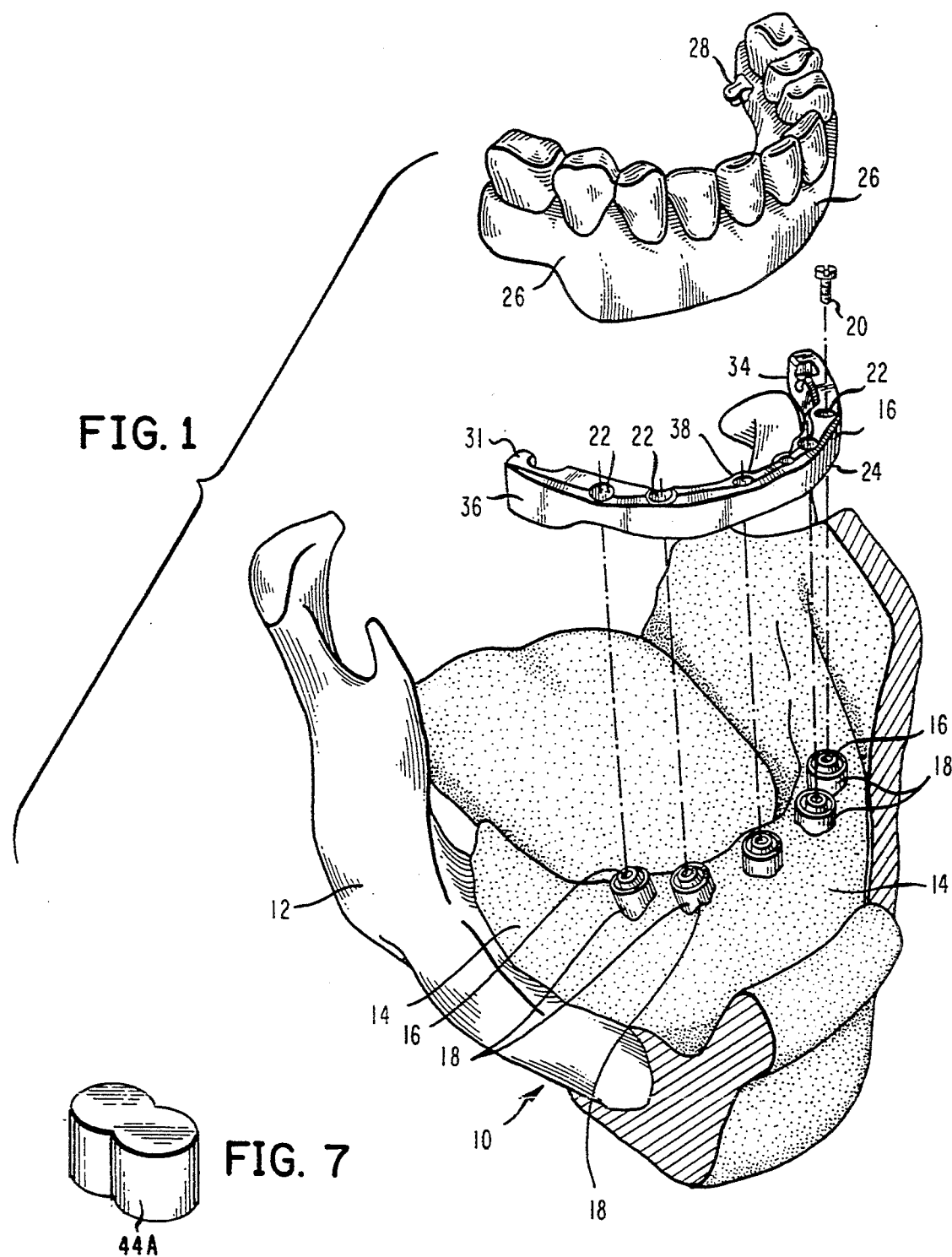
FIG. 1
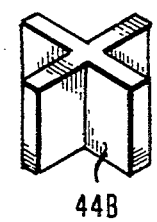
FIG. 7
FIG. 8

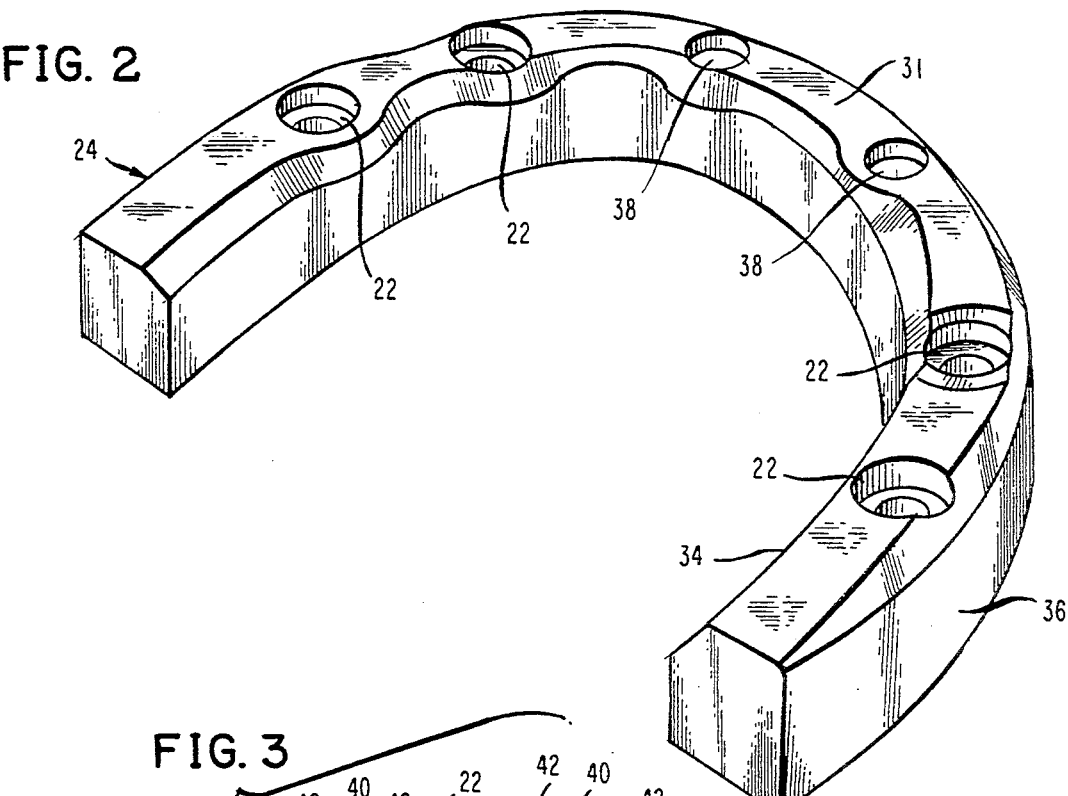
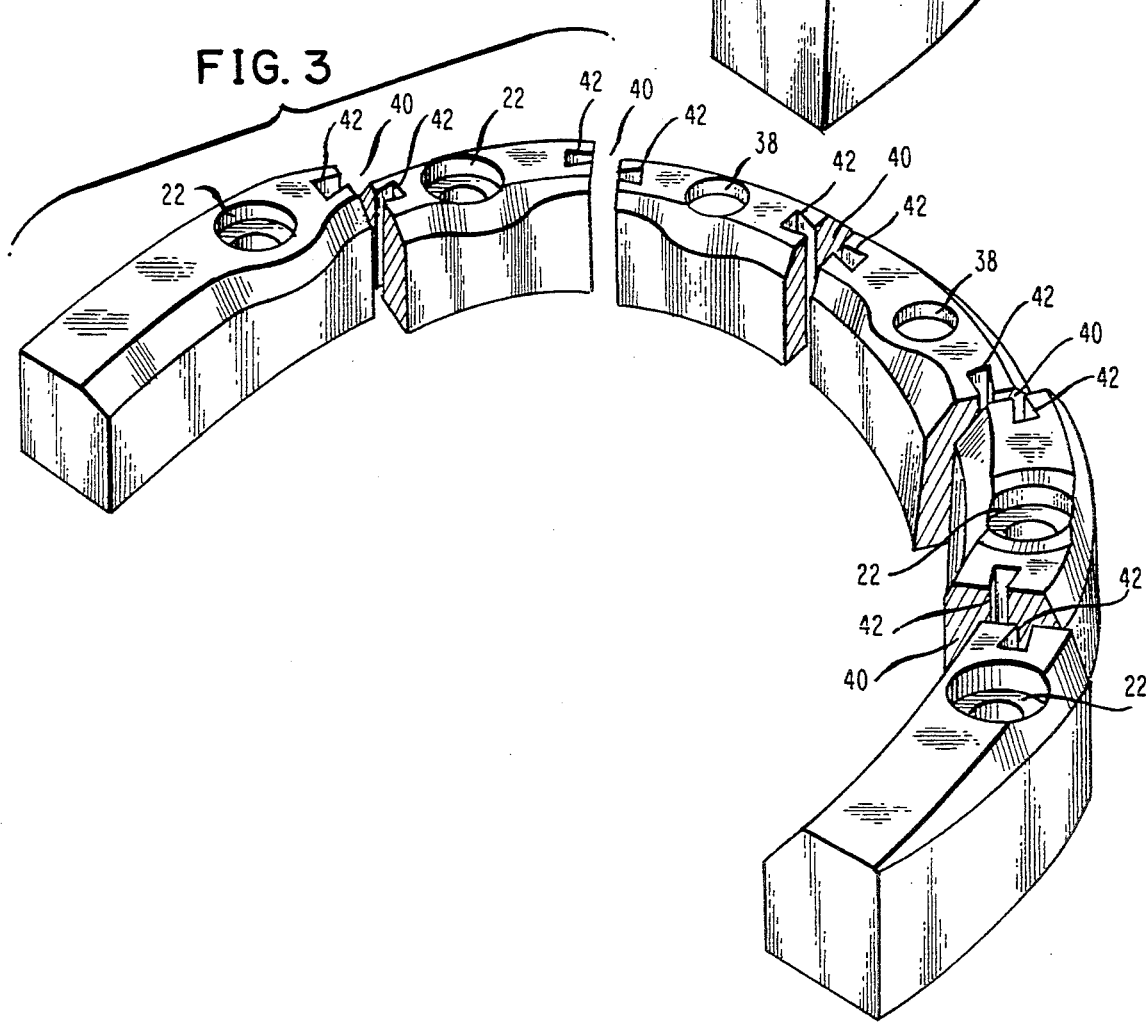

REINFORCED JOINT FOR FITTING DENTAL APPLIANCES AND METHOD FOR FABRICATING SAME

BACKGROUND OF THE INVENTION

1. Field of the Invention

The present invention relates to a dental appliance and, in particular, to a reinforced joint which allows more accurate fitting and installation of the dental appliance by the attending dentist.

2. Description of the Prior Art

In the field of dental prosthetics, there are two (2) major types of dental implant prosthetics which have gained acceptance. The first, commonly known as the over denture, provides for a support structure to be implanted into the alveolar bone, which support structure extends above the gum line and permits the patient to snap-fit the denture into place. This type of construction permits the patient to remove the denture himself and clean the denture and the gum area. The drawback of an over denture is that it does not normally provide sufficient stability under all eating or chewing conditions.

The second type of prosthesis in wide use is that of the fixed prosthesis. Again, support structure is anchored into the alveolar bone, the support structure extending above the gum line and the prosthesis being permanently secured through the support structure into the bone. This type of denture normally provides a more stable denture for the patient, but aesthetic and hygiene problems arise in that the denture can only be removed by a dentist to permit cleaning of the area under the prosthesis and proximate to the support structure. Applicant has improved upon these two types of prosthetics with his fixed removable dental implant system as disclosed in U.S. Pat. No. 4,931,016 and U.S. Pat. No. 5,057,017 which detail the manner in which a fixed removable implant can be fabricated from an electro discharge method (hereinafter EDM).

Applicant has further developed a soldering joint to be used in conjunction with fabricated dental appliances which allows for cooperation between the dental laboratory and the attending dentist in fitting the dental appliance, whether it be a partial bridge or full prosthetic, to the attachment elements. Applicant's reinforced soldering joint permits the attending dentist to accurately adjust the seating of a portion of the dental appliance on each of the attachment elements and to cooperatively secure each segment of the dental appliance to the adjacent segment of the dental appliance which is attached to a similar attachment means. The attending dentist would secure the relationship of the segmented pieces of the dental appliance with a cold set acrylic or other acceptable adhesive in cooperation with diverging recesses formed in adjacent segments of the dental appliance. The diverging recesses having a complimentary plug positioned therein and temporarily secured by the adhesive. The fitted appliance would then be returned to the laboratory where the cold set acrylic or other suitable adhesive would be replaced with a permanent plug joint and solder which would permanently secure the segments of the dental appliance together in a configuration, the accuracy of which, complimentary to the attachment means would be greatly improved over the prior art.

OBJECTS OF THE INVENTION

It is an object of the present invention to provide for a dental implant prosthesis which provides a stable support structure.

It is a further object of the present invention to provide for a dental implant prosthesis which has improved seating charactersistics with respect to the underlying attachments.

It is a still further object of the present invention to provide for a dental implant prosthesis which is structurally secure.

It is a still further object of .the present invention to provide for a dental implant prosthesis in which segments of the dental implant prosthesis are secured together by a novel reinforced joint.

It is a still further object of the present invention to provide for a dental implant prosthesis which permits the more accurate fitting and seating of the prosthesis within the individual's mouth.

SUMMARY OF THE INVENTION

A support structure for a dental implant appliance secured to the alveolar bone, the support structure shaped to the curvilinear contour of the portion of the jaw receiving the dental appliance, the support structure segmented by transverse cuts, each transverse cut having a divergent recess on opposing sides thereof for receipt of a complimentary recess plug in cooperation with investment solder to reattach the segments after fitting.

BRIEF DESCRIPTION OF THE DRAWINGS

The objects and advantages of the invention as well as other objects and advantages will become evident upon consideration of the drawings where:

FIG. 1 is a perspective exploded view of the lower jaw generally illustrating an implant system;

FIG. 2 is a perspective view of the primary support structure for the implant system;

FIG. 3 is an exploded perspective view of the segmented primary support structure for an implant system;

FIG. 7 is a perspective view of an alternative embodiment of the male plug cooperative with the alternative embodiment of the divergent recess;

FIG. 8 is a perspective view of an alternative embodiment of the male plug cooperable with the preferred embodiment of the divergent recesses.

DETAILED DESCRIPTION OF THE DRAWINGS

Figure 4:
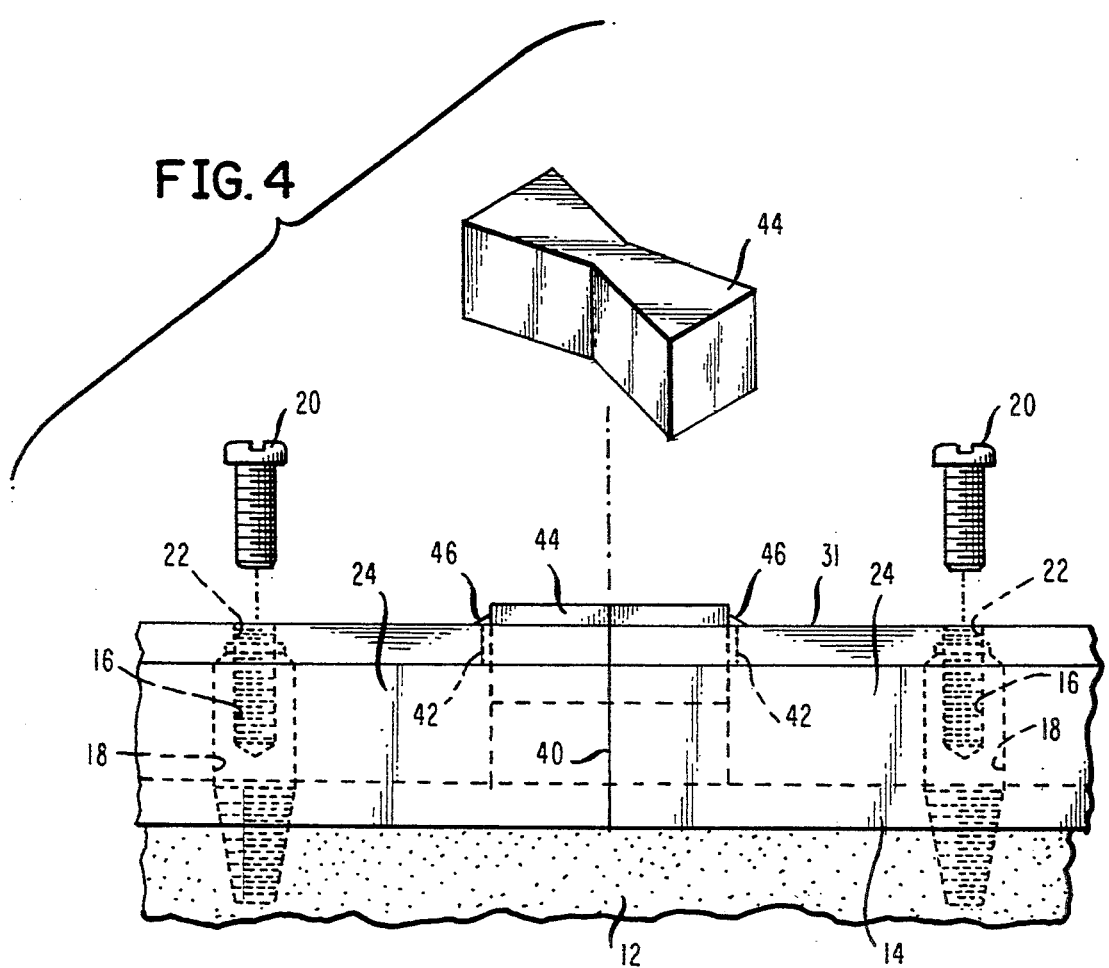
FIG. 4 is a partial cross-sectional view of adjacent segments of the primary support structure secured to the abutment or attachment means to the alveolar bone during fitting.

Referring to FIG. 1, there is an exploded perspective view of an implant system which provides an understanding of the component elements. The examples illustrated herein are with respect to a full implant for the lower jaw of an individual, but it should be understood that the same structure and technique would have application to the upper jaw or to a partial implant, either on the lower or upper jaw. In FIG. 1, the lower jaw 10 is comprised of the alveolar bone 12 which is overlayed by gum tissue 14. The individual whose natural teeth which have been damaged or removed, would opt for a dental implant to provide an aesthetic, yet structurally secure dental prosthesis. The implant would comprise a plurality of attachment means or abutments 18 which would be threadedly secured into the alveolar bone 12 by means of a surgical dental procedure performed in the attending dentist's office. An incision in the gum tissue would be made in order to secure the abutments into the alveolar bone and the gum tissue would be allowed a period of healing after such attachment such that the gum tissue would conform to the outer circumferential shape of the abutments. Each abutment would have formed therein, a threaded recess 16 for cooperation with a fastener 20 which would pass through an aperture 22 in the primary bar 24 in order to secure the primary bar 24 to the abutments.

The primary bar 24 serves as the support for the supra structure 26 which comprises the acrylic teeth or denture which is removably secured to the primary bar 24 by means of a locking means 28.

The manner in which the primary bar and supra structure 24 and 26 are fabricated by means of the electro erosion method (EDM) is detailed in the aforesaid patents which have issued to Applicant.

Applicant has developed a further refinement of the fitting technique in order to ensure the proper seating of the primary bar 24 with the abutments 18 which permits the attending dentist to perform fine tuning adjustments of the primary bar as it is seated on the abutments which will eliminate any discomfort to the patient once the primary bar is secured to the abutments and which improves the seating of the primary bar on the abutments without degrading the structural integrity of the primary bar.

FIG. 2 is a perspective view of the primary bar 24. It has a substantially flat top surface 31 and tapered sidewalls 34 and 36. The buccal and lingual tapered sidewalls 34 and 36, respectively, are preferably tapered from 0° to 10° from the vertical to aid in the fabrication process for fitting the primary bar 24 to the supra structure 26. The plurality of apertures 22 are formed in top surface 31 of primary bar 24 for cooperation with the fastener 20 which would be threadedly secured in threaded recess 16 of abutment 18.

Top flat surface 31 of primary bar 24 may also contain guide post apertures 38 which align with depending guide posts (not shown) on the underside of supra structure 26, for aligning the supra structure with the primary bar when the supra structure is to be secured to the primary bar either by the individual or by the dentist.

FIGS. 1 and 2 illustrate a one-piece primary bar 24 for attachment to abutments 18 which would be utilzed to replace all of the individual's teeth on the lower jaw. As was pointed out in U.S. Pat. No. 5,057,017, it sometimes became necessary to fabricate the primary bar 24 in segments so as to be discontinuous as opposed to being of a single piece construction. This procedure was oftentimes dictated by the parameters of the patient's mouth which required the fabrication in sections with each section being secured to the respective abutments 18.

Applicant's present invention would also segment primary bar 24 as illustrated in FIG. 3 by performing a transverse cut 40 of primary bar 24 between each of adjacent apertures 22 and guide post apertures 38. A diverging recess 42 would then be electrically eroded on opposing sides of the transverse cut 40. These steps would be performed in the dental laboratory. The attending dentist would then secure each segmented portion of primary bar 24 to its respective abutment 18 utilizing a fastener 20. The attending dentist would check the seating of each segment of primary bar 24 and its angular and alignment relationship with each adjacent section of primary bar 24. Then a plug 44 would be inserted into the adjacent diverging recesses 42 so as to position adjacent segments of primary bar 24 as illustrated in FIG. 4. The attending dentist would then use a cold set acrylic 46 or other suitable adhesive to secure the plug and hence the two adjoining segments of the primary bar 24, in position. This process would be repeated with respect to each segment of the primary bar 24. When completed, the attending dentist would have resecured the segmented primary bar 24 by means of the plugs 44 and the cold set acrylic 46 or other adhesive. Each segment of the primary bar would now have been accurately seated with respect to its respective abutment 18 and angularly and/or alignably positioned with each adjacent segment of primary bar 24 and secured to each adjacent section of primary bar 24.

Figure 6:
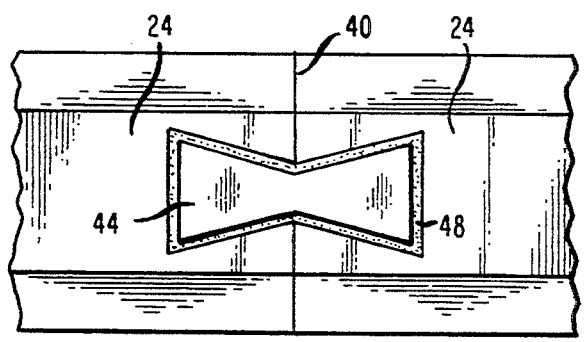
FIG. 6 is a partial top view of adjacent segments of the primary support structure after attachment.
Figure 5:
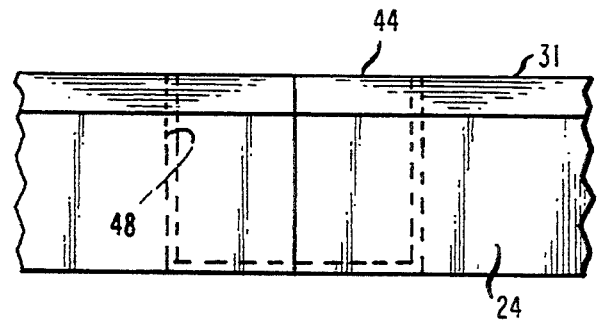
FIG. 5 is a partial side view of adjacent segments of the primary support structure after being resecured at the dental laboratory.

The attending dentist would then forward the primary support bar which is now temporarily resecured by means of the plug 44 and cold set acrylic 46 to the dental laboratory. The dental laboratory would then dissolve or melt the cold set acrylic 46 away from the plug 44 without disturbing the positioning of plug 44 or the relationship between adjoining segments of primary support bar 24, and simultaneously invest solder 48 into the female diverging recesses 42 in support bar 24 and any spacial openings which may exist between plug 44 and the sidewalls of the cuts 42 in primary support bar 24. FIG. 5 illustrates a partial side view and FIG. 6 a top view of adjacent segments of primary support bar 24 resecured in such a manner. The laboratory would ensure that the upper surface 31 of primary support bar 24 would be smooth and cooperative with the underside of supra structure 26. To that end, plug 44, when temporarily secured by the attending dentist, may extend above the upper surface 31 of primary support bar 24 to permit ease of fitting. The dental technician at the dental laboratory would shave off or reduce any protrusion of plug 44 which might extend above upper surface 31 of primary support bar 24.

The segmentation of the primary support bar 24 and its resecuring by means of the plug 44 allows the attending dentist the greater flexibility in fitting the implant or bridge to the abutment or attachment means 18 in ensuring accurate seating and secure fastening of the primary support bar 24 to the abutment means 18 by means of the fastening means 20. This will therefore allow for correction of any inaccuracies which may have arisen from the initial impression taken by the dentist and any inaccuracies or dimensional problems which might exist with respect to the fastening means 20 or the abutments 18. It translates into a more secure implant or bridge for the patient which will not only be more aesthetically pleasing, but will ensure more confidence in the patient due to the accurate manner in which it is secured in the patient's mouth.

In the examples illustrated herein, the diverging recesses 42 eroded in the support bar are illustrated as female dovetail recesses. Plug 44, as illustrated, is shown to be a double male dovetail which is substantially coincidental with the female dovetail diverging recesses. The dovetail recesses and dovetail plug have been used for illustrative purposes. Alternative shaped recesses and plugs could be utilized without diverting from the spirit and scope of the invention. The essential detail is that the recesses are cooperable with the plug and the adhesive in fitting the dental appliance and that the recesses and plug are cooperable when invested with solder so as to provide strength to the support bar.

In regard to alternative embodiments of the divergent recesses, FIG. 7 illustrates a second embodiment of a divergent recess 42. In this instance, the divergent recess 42 and plug 44A resemble a figure eight with partial circular recesses being eroded into each adjacent segment of the primary bar.

FIG. 8 illustrates an alternative embodiment of plug 44 for use with the preferred divergent recess 42 which is in the form of a female dovetail. In this instance, a solid male dovetail plug is not required, but rather, a plug 44B, being X shaped in cross section, would suffice to secure adjacent segments of the primary bar when positioned within the divergent recesses and invested with solder.

While the present invention has been described in connection with the exemplary embodiment thereof, it will be understood that many modifications will be apparent to those of ordinary skill in the art; and that this application is intended to cover any adaptations or variations thereof. Therefore, it is manifestly intended that this invention be only limited by the claims and the equivalents thereof.

What is claimed is:

1. A primary support structure for a dental implant appliance, said support structure securable to an attachment means secured to the alveolar bone, said primary support structure comprising:

a support bar shaped to the curvilinear contour of the portion of the jaw receiving said dental appliance, said support bar having a plurality of apertures therethrough for receipt of a fastening means cooperative with an attachment means to secure said support bar to said attachment means, said support bar segmented by transverse cuts between said adjacent apertures in said support bar, each of said transverse cuts having a divergent recess on opposing sides of said cuts, a complimentary recess plug complimentary with said opposing divergent recesses and cooperative with invested solder for rejoining adjacent segments of said support bar after fitting of adjacent segments to said attachment means.

2. The primary support structure for a dental implant appliance in accordance with claim 1 wherein said adjacent divergent recesses are formed by electrical erosion and are shaped in the form of a female dovetail.

3. The primary support structure for a dental implant appliance in accordance with claim 2 wherein said complimentary recess plug is double dovetailed in cross sectional area to cooperate with said female dovetail recess.

4. The primary support structure for a dental implant appliance in accordance with claim 2 wherein said complimentary recess plug is X shaped in cross sectional area to cooperate with said female dovetail recess.

5. The primary support structure for a dental implant appliance in accordance with claim 1 wherein said adjacent divergent recesses are figure 8 shaped in cross sectional area and said complimentary recess plug is figure 8shaped in cross sectional area to cooperate with said divergent recess.

6. The primary support structure for a dental implant appliance in accordance with claim 1 wherein said transverse cuts are preferably equidistant between said adjacent apertures.

7. The primary support structure for a dental implant appliance in accordance with claim 1 wherein said complimentary recess plug coopoerable with said invested solder conforms to the original surface of the support bar prior to segmentation.

8. A method for fitting the primary support structure of a dental implant appliance to the attachment means in the form of abutments secured to the alveolar bone, the method comprising:

a. shaping the support bar to the curvilinear contour of the portion of the jaw receiving the dental appliance;
   b. forming and aligning the apertures in the primary support structure with the attachment means in the form of abutments secured in the alveolar bone;
   c. segmenting the primary support structure between said plurality of apertures by electrical erosion;
   d. forming divergent recesses in said primary support structure in adjacent segments of said primary support structure immediately adjacent said transverse cuts;
   e. fitting said segments of said primary support structure to said abutments and securing to said abutments by appropriate attachment means;
   f. positioning said adjacent segment of said primary support structure on said adjacent abutment and securing said segment to said abutment;
   g. aligning and adjusting said adjacent segments for proper fit;
   h. securing said adjacent segments in alignment by means of a complimentary recess plug positioned in said divergent recesses;
   i. temporarily securing said complimentary recess plug by a temporary adhesive;
   j. repeating steps e through i until said segments of said primary support structure have been temporarily resecured;
   k. removing said reattached primary support structure from the patient's mouth;
   l. removing said temporary adhesive from said primary support structure and contemporaneously introducing permanent adhesive to said divergent recesses about said recess plug;
   m. finishing said surface of said primary support structure to present a smooth continuous surface.

* * * * *